(12) United States Patent
Verin et al.

(10) Patent No.: US 7,393,359 B2
(45) Date of Patent: Jul. 1, 2008

(54) EXPANDABLE MULTI-LAYER TUBULAR STRUCTURE AND PRODUCTION METHOD THEREOF

(75) Inventors: Vitali E. Verin, Chêne-Bourge (CH); Igor I. Papirov, Kharkov (UA)

(73) Assignee: Endosense SA (CH)

( * ) Notice: Subject to any disclaimer, the term of this patent is extended or adjusted under 35 U.S.C. 154(b) by 346 days.

(21) Appl. No.: 10/524,176

(22) PCT Filed: Jul. 25, 2003

(86) PCT No.: PCT/EP03/08218
§ 371 (c)(1),
(2), (4) Date: Mar. 7, 2005

(87) PCT Pub. No.: WO2004/017864
PCT Pub. Date: Mar. 4, 2004

(65) Prior Publication Data
US 2006/0053618 A1   Mar. 16, 2006

(30) Foreign Application Priority Data
Aug. 16, 2002   (EP) ................................. 02405698

(51) Int. Cl.
*A61F 2/06* (2006.01)
(52) U.S. Cl. ..................................................... 623/1.44
(58) Field of Classification Search ........ 623/1.11–1.48
See application file for complete search history.

(56) References Cited

U.S. PATENT DOCUMENTS

| 5,630,806 | A | 5/1997 | Inagaki et al. |
| 5,873,904 | A * | 2/1999 | Ragheb et al. ............. 623/1.13 |
| 6,261,320 | B1 | 7/2001 | Tam et al. |
| 6,383,214 | B1 | 5/2002 | Banas et al. |
| 6,849,085 | B2 * | 2/2005 | Marton ...................... 623/1.13 |
| 2001/0044652 | A1 * | 11/2001 | Moore ........................ 623/1.16 |
| 2002/0062147 | A1 * | 5/2002 | Yang ......................... 623/1.13 |
| 2005/0060021 | A1 * | 3/2005 | O'Brien et al. ............ 623/1.15 |

* cited by examiner

*Primary Examiner*—Suzette Gherbi
(74) *Attorney, Agent, or Firm*—Gerald E. Hespos; Anthony J. Casella

(57) ABSTRACT

The invention relates to a radially expandable multi-layer tubular structure which is intended to be used as a stent and to the production method thereof. The inventive structure comprises an outer layer (1) and an inner layer (2) which are solidly connected to one another. One of the aforementioned layers (2) is provided with hollow channels (3) through the thickness thereof while the other layer is provided with perforations (4). Said channels (3) can be used to alter the mechanical properties of the stent and to house a medicament for the local treatment of the vessel in which the stent is disposed.

13 Claims, 2 Drawing Sheets

EXPANDABLE MULTI-LAYER TUBULAR STRUCTURE AND PRODUCTION METHOD THEREOF

This application is a 371 filing of PCT/EP2003/008218 filed Jul. 25, 2003 and published Mar. 4, 2004 under publication WO 2004/017864 and claims priority benefits of European Patent application No. 02405698.8 filed Aug. 16, 2002.

BACKGROUND OF THE INVENTION

1. Field of the Invention

The present invention relates to an expandable multilayer tubular structure intended to be used as a stent, comprising at least two layers firmly attached to each other, and also to a process for manufacturing it.

It has been known for many years to use implantable devices for the treatment of certain diseases in humans or animals. Thus, such a device has been partly or completely inserted into the esophagus, the trachea, the colon, the vascular system, the urinary tract, etc. In the vascular system, when it is desired to introduce such a device, usually called a stent, we require a catheter, a balloon and a filiform guide or the like.

2. Description of the Related Art

The device, when it is positioned at the place where the treatment has to be carried out, extends radially in order to support the vessel walls. Depending on the desired treatment, the stent must remain in place or be removed after the period of treatment. Certain stents that remain in place are provided with a medicinal product that must diffuse over a certain period of time so as, on the one hand, to treat the lesion and, on the other hand, to remedy the lesions that may occur by the fact that the vessel, upon inserting the stent, has been disturbed. The stent, especially one that has to remain inside the tube, must have certain almost contradictory mechanical properties, namely it has to be small, lightweight and, above all, after having been radially relaxed, it must withstand the pressure of the walls of the vessel or tube inside which it is placed, without collapsing. It is therefore necessary, on the one hand, for it to be sufficiently rigid and strong, radially, in order to prevent inopportune collapse and, on the other hand, it must be able to be expandable so that it occupies the place that is necessary for the treatment inside the human or animal vessel or tube.

SUMMARY OF THE INVENTION

The object of the present invention is to propose such a device which, on the one hand, exhibits good mechanical properties, going in the aforementioned direction, and, on the other hand, if desired, it may contain a medicinal product for diffusion at the point of treatment.

The benefit of this multilayer structure is the fact that it consists of at least two different layers that may possibly have mechanical properties that differ by their nature, but above all by their structure, namely the fact that one of the layers, preferably the layer located on the inside, is provided with recesses that give mechanical properties that differ from the other layer.

Depending on the embodiments, one of the layers, preferably the outer layer, may also be provided with radial perforations, the purpose of which is, above all when the stent includes a medicinal product, to allow it to diffuse to the outside.

According to another embodiment, the recesses are directed either toward the inside of the layer located on the inside, or toward the outside, depending on the desired use.

According to another embodiment, the structure comprises at least three layers, at least one of which is preferably provided with radial perforations.

The invention also relates to the process for manufacturing such a stent.

In one aspect of the invention, the structure is manufactured starting from two metal sheets in order to form the tube that will result in the stent, whereas, another aspect of the invention, the process starts with two metal tubes, the outside diameter of one of which is slightly smaller than the inside diameter of the other so that it is possible for one of the tubes to slide in the other. The various formation steps, however, are almost identical.

BRIEF DESCRIPTION OF THE DRAWINGS

Preferred embodiments of the invention will be described below with the aid of the appended drawings wherein.

DETAILED DESCRIPTION OF THE PREFERRED EMBODIMENTS

Figure 1:
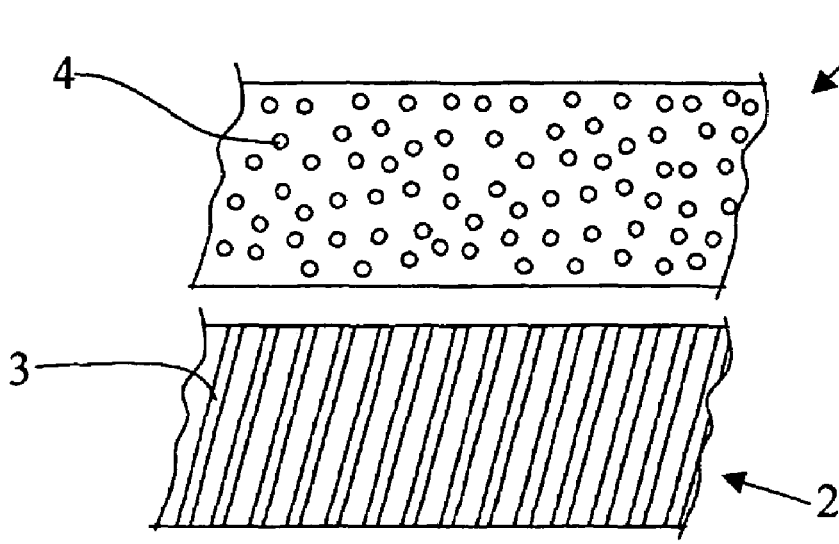
- FIG. 1 shows two metal sheets in perspective.

FIG. 1 shows two metal sheets 1 and 2 that may be chosen from biocompatible materials of the type comprising Ta or 316L steel or 40% Elgiloy, Pt/Ir alloy, etc. The thickness of these sheets is around 50 microns. Recesses are etched on the surface of sheet 2, which will constitute the inner layer of the stent. These recesses may be in the form of straight lines or any other configuration. Provision may be made for these lines to form periodic patterns, the period of which is around 50 to 60 microns. Their depth may be around 40% of the thickness of the sheet, i.e. about 20 microns.

Sheet 1, which will constitute the outer layer, is provided, in the present case, with perforations 4, but it is also possible to leave it as it is. The thickness of the sheet 1 is also around 50 microns. The sheets 1 and 2 may be made from two different materials, depending on the mechanical results that it is desired to obtain. Subsequently, the two surfaces of the two sheets, which will be placed one against the other, are treated in order to allow the two sheets to bond together so as to constitute in practice a single part and so that they cannot be separated during the subsequent manufacturing steps. The two surfaces may be treated by sandblasting or with a plasma, or by any other similar method, allowing intimate bonding to be achieved when the sheets are placed against each other with their two surfaces facing each other.

According to a preferred embodiment, it is possible to deposit, on one of the treated surfaces, a metal layer with a maximum thickness of 1 micron so as to improve the bonding between the two surfaces.

The two sheets, with the two faces against each other, are then superposed and the structure thus obtained undergoes hot vacuum rolling. Next, meshing specific to the stent is formed by machining, for example using a laser or other similar process, that is to say holes are formed that pass through both layers. The structure thus obtained is then bent so as to form a tube, which is welded, for example by laser welding, along the generatrix, and then it is cut to the desired length in order to form the stents. The stent obtained may, for example, may be that shown in FIG. 6, which shows only one variant of the meshing of known stents.

If desired, the hollows that remain, which correspond to the recesses in the thickness of the lower layer, or even the perforations, may be filled with a medicinal product or combination of medicinal products, which will subsequently diffuse out at the place of the treatment.

Figure 2:
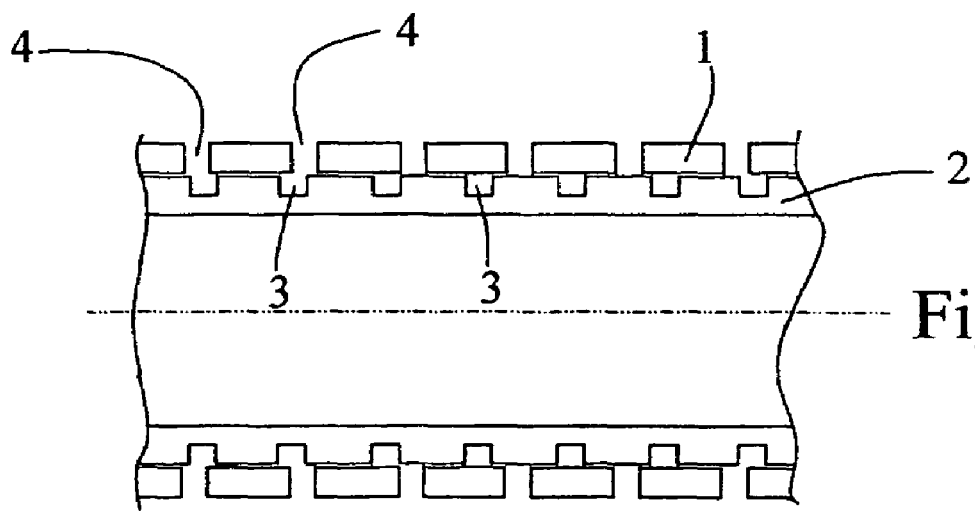
- in FIGS. 2 and 3 we have shown two variants of a tube formed from the two sheets of FIG. 1, but before the machining in order to obtain the stent-type meshing.
Figure 3:
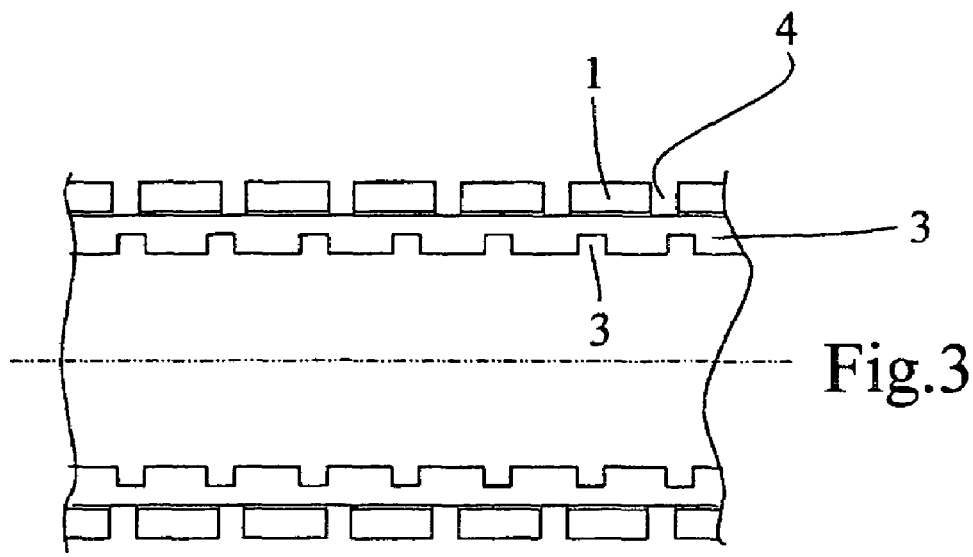

There are two ways of forming the stent in the present case and, in particular during assembly of two sheets one against the other, it is possible to join them either as shown in FIG. 2, by treating the surface of sheet 2 provided with the recesses 3 and joining them to the treated surface of the upper sheet 1, or, as in FIG. 3, the recesses are directed toward the inside of the stent.

The stent thus obtained exhibits good characteristics of radial resistance to collapse and also the possibility of radial expansion, which qualities are needed for a stent. This is because, during rolling, the yield strength of each layer increases as the thickness of this layer decreases, thereby improving the aforementioned qualities of the stent. It turns out that, by rolling a structure of the "sandwich" type with a given thickness, a yield strength is obtained that is greater than the yield strength obtained after rolling a single layer having the same thickness as the "sandwich" structure. For this reason, it is possible to apply, by analogy, the same manufacturing process using at least three layers, at least one of which is preferably provided with radial perforations and the others with recesses.

Figure 4:
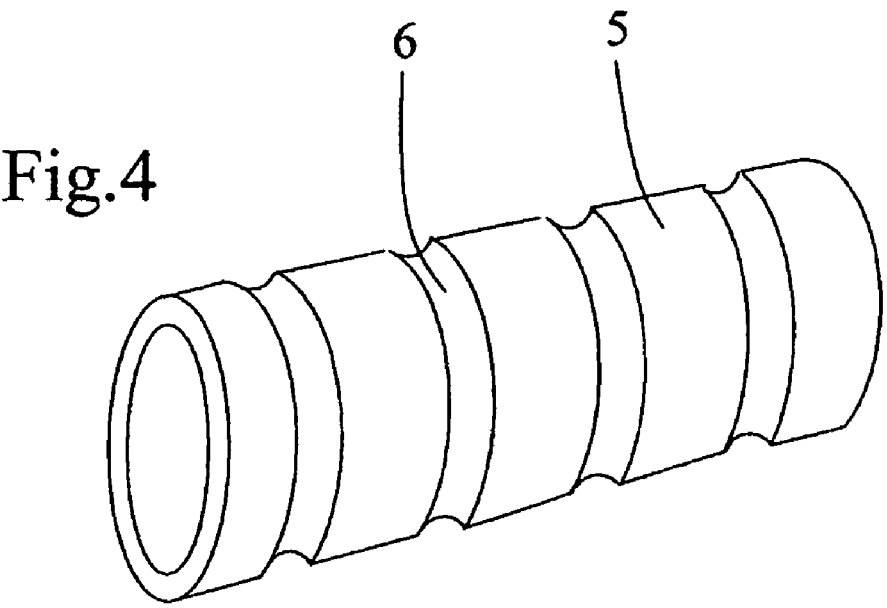
- in FIG. 4 we have shown in perspective, a variant of the inner tube, and according to the other embodiment of the process, and
- in FIG. 5 the outer tube; and
- in FIG. 6 we have shown, in side view, a known representation of a stent-type meshing.
Figure 5:
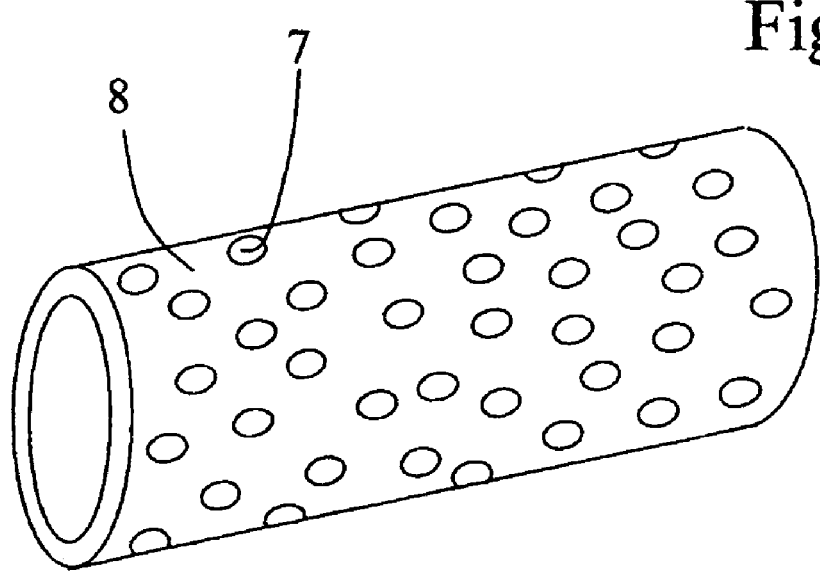

In FIGS. 4 and 5 we have shown two tubes that also have a thickness of around 50 microns. The tube 5, which will be the inner tube, has an outside diameter slightly less than the inside diameter of the tube 8, so that the tube 5 can slide in the tube 8. As previously, the outer surface of the tube 5 is provided with recesses 6 that may have different shapes, for example rings, circles or ellipses, or any other similar figure, the depth of the recesses always being determined according to the desired mechanical properties. The depth may be around 40% of the thickness of the wall of the tube, i.e. about 20 microns. Next, this surface is treated by sandblasting or with a plasma, or by any other similar method, so that it is possible thereafter to achieve intimate bonding between the two tubes.

The tube 8 may be provided with radial perforations 7. After the outer surface of the tube 5 has been treated, the tube 5 is slid into the tube 8 and the tubes are hot drawn under vacuum so as to achieve mechanical bonding of the two tubes, forming a single element with no risk of them subsequently coming apart. It is also possible, as in the previous case, to deposit, on the outer surface of the tube 5, a layer of metal with a maximum thickness of 1 micron so as to facilitate this bonding between the two surfaces, namely the inner surface of the tube 6 and the outer surface of the tube 5.

Figure 6:
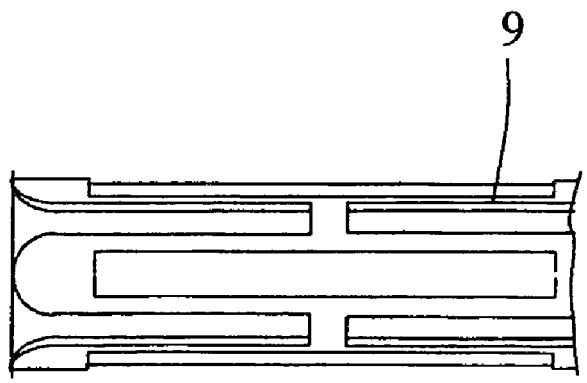

Next, the tube obtained after drawing is machined by known means, such as laser machining, chemical etching, etc. in order to obtain meshing of the stent type, such as, for example, that shown in FIG. 6. It is sufficient thereafter to cut the tube thus obtained to the desired length in order to obtain stents. The properties of these stents are the same as those obtained above by any very similar means, the only difference being the fact that we start from two metal sheets rather than two tubes. In the present case, it is also possible to fill the recesses 6 and the optional perforations 7 with a medicinal product so that it subsequently diffuses out when the stent has been placed in the body. As mentioned above, the materials used for the two tubes may be chosen from those mentioned above, it being possible for the two tubes to be made of the same material or of two different materials, so as to benefit from their mechanical properties associated with their nature and particular form.

The above comment relating to increasing the yield strength also applies to this embodiment and structures may be provided that are composed of at least three layers by applying the same process by analogy.

The invention claimed is:

1. A radially expandable multilayer tubular structure intended to be used as a stent, comprising at least inner and outer layers, each of the layers being formed from a metal or metal alloy, and each having opposite inner and outer surfaces, the outer surface of the inner layer being secured in substantially face-to-face engagement with the inner surface of the outer layer to define an integral metal-to-metal bond therebetween, recesses being formed in one of the inner and outer surfaces of the inner layer and extending partly towards the other of the inner and outer surfaces of the inner layer, the outer layer being formed with an array of radial perforations extending entirely therethrough from the inner surface to the outer surface thereof, the recesses being filled with a medicinal product.

2. The structure as claimed in claim 1, wherein said recesses are located on the inner surface of said inner layer.

3. The structure as claimed in claim 1, wherein said recesses are located on the outer surface of the inner layer.

4. The structure as claimed in claim 1, wherein the material used for said layers is Ta or 316L steel or Elgiloy (40%), or a Pt/Ir alloy, or any other biocomplete metal or alloy.

5. The structure as claimed in claim 1, wherein the structure comprises at least three layers.

6. A process for manufacturing radially expandable multilayer tubular structure intended to be use as a stent, the process comprising the following steps:
   providing first and second metal sheets, each of the sheets having opposite first and second surfaces;
   forming recesses on one of the surfaces of first sheet;
   treating one of the surfaces of each sheet by sandblasting or with a plasma;
   superposing the sheets with their treated faces against each other and hot vacuum rolling to bond the sheets in face-to-face relationship;
   machining of the combination of the two bonded sheets in order to obtain meshing specific to the stents;
   forming of a tube by rolling up the sheets and welding along the generatrix forming the seam; and
   cutting of the tube to a desired length in order to obtain stents.

7. The process as claimed in claim 6, further comprising forming perforations through the second sheet before the treatment of one of its surfaces.

8. The process as claimed in claim 7, wherein the said perforations form periodic patterns, the period of which is from 50 or 60 microns.

9. The process as claimed in claim 6, further comprising depositing a thin layer of a metal with a maximum thickness of 1 micron to the outer surface of the second tube after the outer surface of the second tube has been treated by sandblasting or with plasma for improving intimate bonding of the tubes and to prevent the two tubes from separating.

10. The process as claimed in claim 6, wherein the recesses are filled with a medicinal product.

11. The process as claimed in claim 6, wherein the recesses form periodic patterns, the period of which is from 50 to 60 microns.

12. A process for manufacturing a radially expandable multilayer tubular structure intended to be use as a stent, comprising:

providing a first metal tube and a second metal tube, the outside diameter of the second metal tube being less than the inside diameter of the first, each of the tubes having opposite inner and outer surfaces, recesses being formed in the outer surface of the second tube;

treating the outer surface of the second tube by sandblasting or with a plasma;

sliding the second tube into the first tube to form a tube assembly;

subjecting the tube assembly to hot drawing under vacuum to form a single tube;

machining the single tube to form a structure having a meshing specific to the stents; and cutting the machined tube to a desired length in order to obtain stents.

13. The process as claimed in claim 12, further comprising forming perforations through the first tube before the second tube is slid into the first tube.

* * * * *